(12) United States Patent
Liu et al.

(10) Patent No.: US 8,153,441 B2
(45) Date of Patent: Apr. 10, 2012

(54) METHOD FOR ANALYZING STRUCTURE AND PURITY OF SEROTONIN TRANSPORTER IMAGING AGENT [$^{123}$I] ADAM AND PRECURSOR SNADAM

(75) Inventors: Kung-Tien Liu, Taoyuan County (TW); Hang-Hsing Yang, Taoyuan County (TW); Yi-Chih Hsia, Taoyuan County (TW); Chang-Yung Su, Taoyuan County (TW); Tai-Sheng Lin, Taoyuan County (TW); Chia-Chieh Chen, Taoyuan County (TW); Lie-Hang Shen, Taoyuan County (TW)

(73) Assignee: Institute of Nuclear Energy Research Atomic Energy Council, Taoyuan County (TW)

( * ) Notice: Subject to any disclaimer, the term of this patent is extended or adjusted under 35 U.S.C. 154(b) by 172 days.

(21) Appl. No.: 12/605,210

(22) Filed: Oct. 23, 2009

(65) Prior Publication Data
US 2010/0112706 A1  May 6, 2010

(30) Foreign Application Priority Data
Oct. 31, 2008 (TW) .............................. 97142127 A

(51) Int. Cl.
*G01N 24/00* (2006.01)

(52) U.S. Cl. .......................................... 436/173; 436/56
(58) Field of Classification Search ........................ None
See application file for complete search history.

(56) References Cited

OTHER PUBLICATIONS

Liu et al., "Structure elucidation and purity assay of ADAM by HPLC and LC-ESIMS/MS", J. Nucl. Med. 2007; v.48, (Sipplmental 2), p. 323P, Abstract.*
Barceló "Influence of Reversed- and Normal-phase Liquid Chromatographic Eluents in the Fragmentation of Selected Chlorinated Herbicides in Thermospray Liquid Chromatography-Mass Spectrometry", Org. Mass Spectrometry, 1989, v. 24, pp. 898-902.*
"Introduction to MS Quantitation and Modes of LC/MS Monitoring" (IonSource), no date http://www.ionsource.com/tutorial/msquan/intro.htm.*
Shunichi Oya et al., 2-((2-((Dimethylamino)Methyl)phenyl)thio)-5-iodophenylamine (ADAM): An Improved Serotonin Transporter Ligand, Nuclear Medicine & Biology, Jan. 2000, pp. 249-254, vol. 27, Elsevier Science Inc., Philadelphia.

* cited by examiner

*Primary Examiner* — Yelena G Gakh
(74) *Attorney, Agent, or Firm* — Morris Manning & Martin LLP; Tim Tingkang Xia, Esq.

(57) ABSTRACT

An analytical technique for determining the structures of serotonin transporter (SERT) imaging agent [$^{123}$I] ADAM and its precursor, SnADAM by using a high-performance liquid chromatography tandem mass spectrometer (LC-MS/MS) is provided. An analytical technique for determining the purity of SnADAM by using a high-performance liquid chromatograph (HPLC) is also provided.

3 Claims, 13 Drawing Sheets

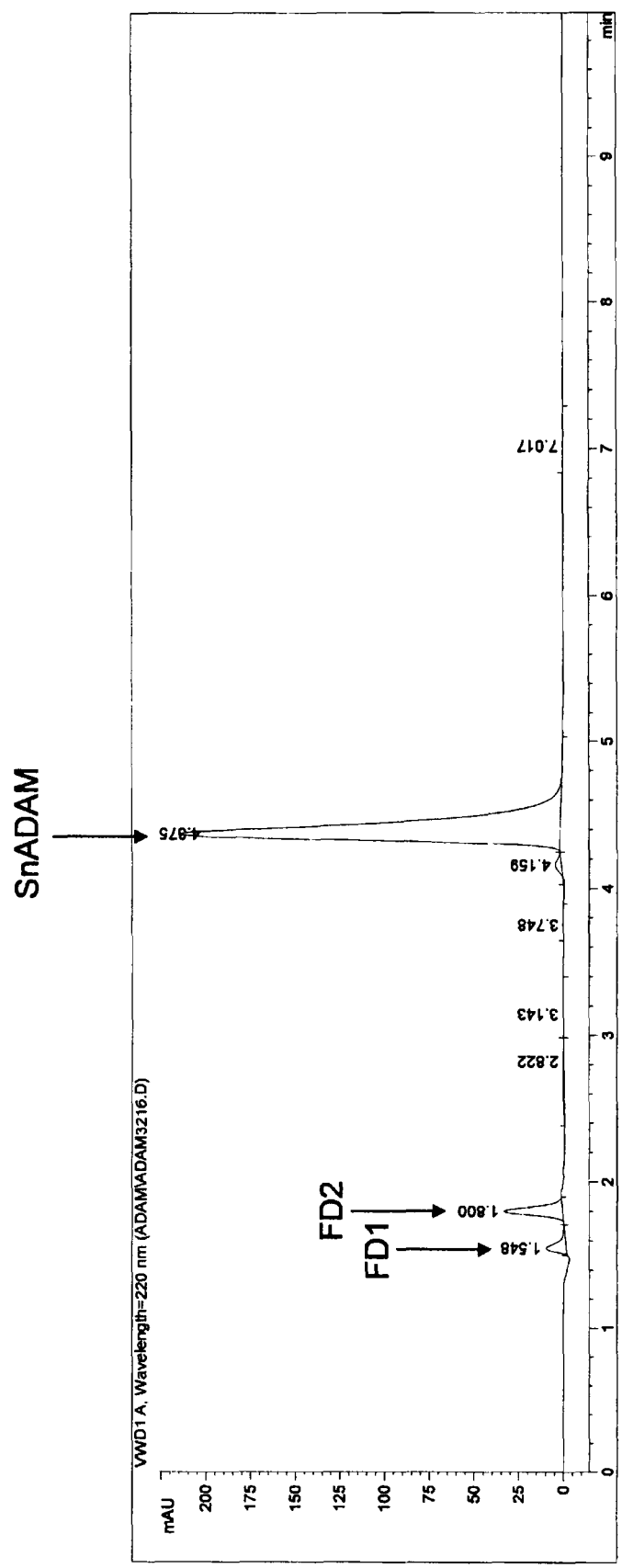
FIG. 3A 1.0M HCl for 30 mins

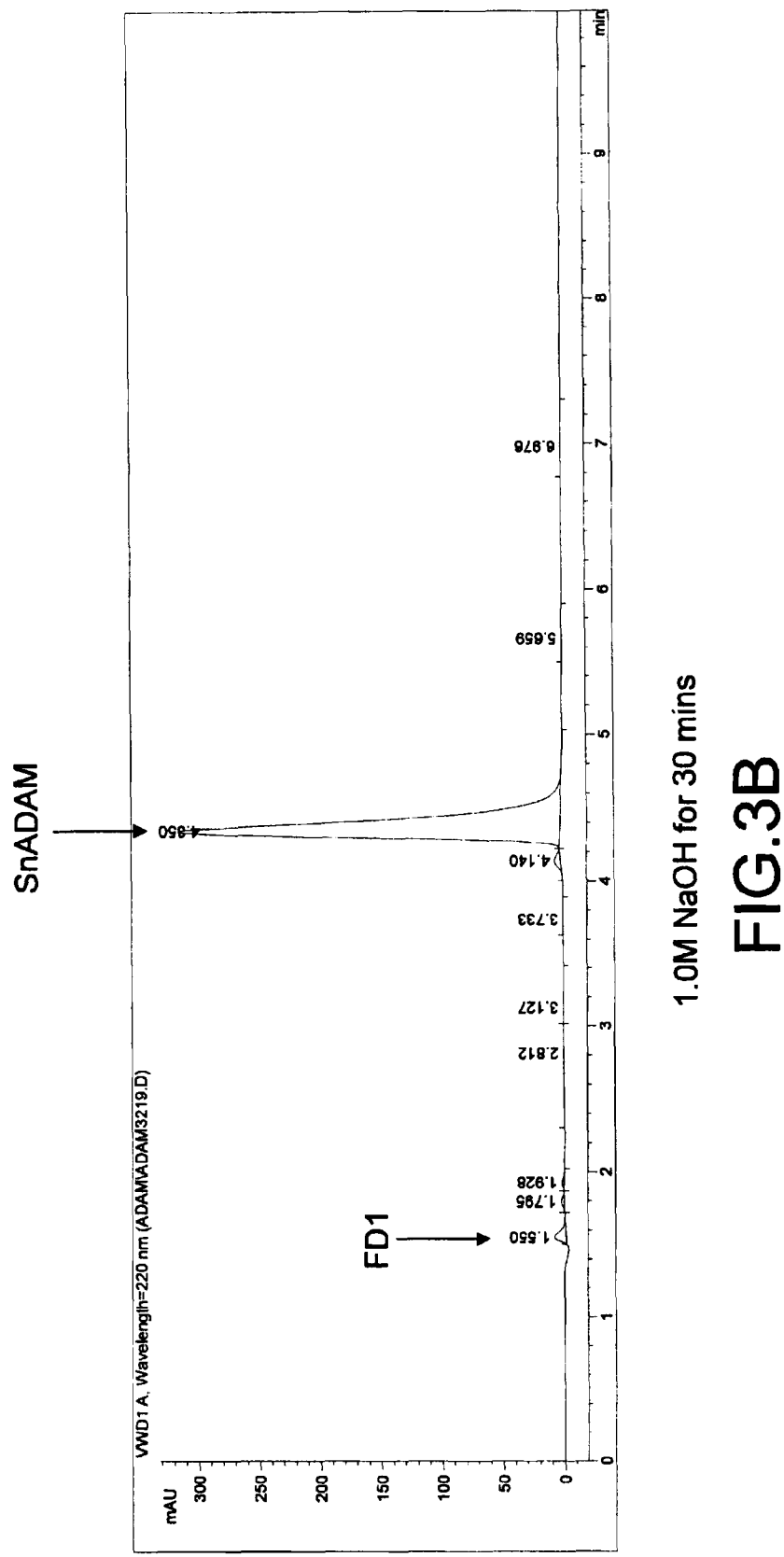

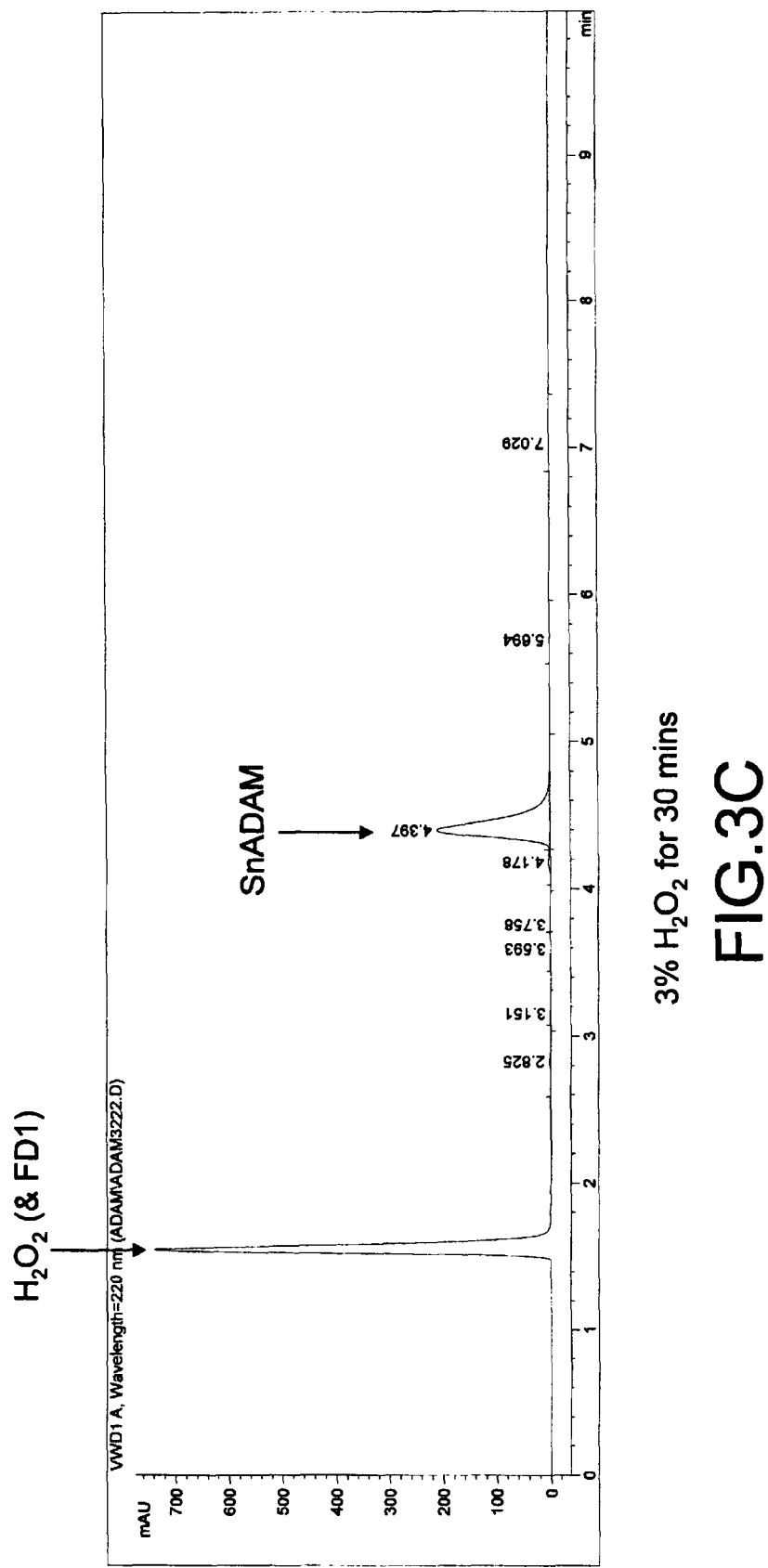

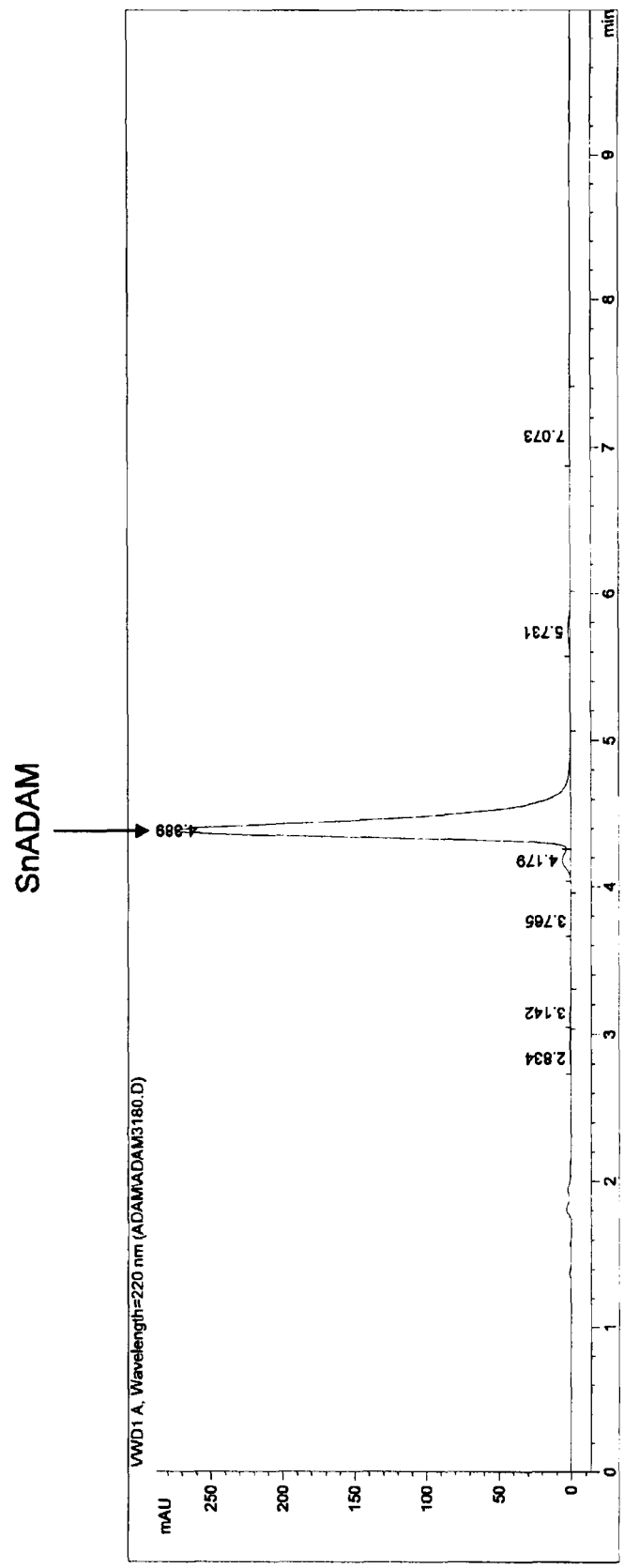
FIG.3D 80°C for 30 mins

METHOD FOR ANALYZING STRUCTURE AND PURITY OF SEROTONIN TRANSPORTER IMAGING AGENT [$^{123}$I] ADAM AND PRECURSOR SNADAM

BACKGROUND OF THE INVENTION

1. Field of the Invention

The present invention relates to a method for analyzing the structure of a serotonin transporter (SERT) tracer, and more particular, to a method for analyzing fragmented structures of [$^{123}$I]ADAM and precursor thereof, SnADAM, and an analytical method for determining the purity of SnADAM.

2. Related Art

Serotonergic neuronal function plays an important role in the central nerve system. Serotonin is mainly produced in the region of the raphe nuclei, and then projected to other brain regions, such as olfactory bulb, cerebral cortex, hippocampus, and basal ganglia. Serotonin transporters (SERTs) are macromolecular complexes and located in the semipermeable membrane of serotonergic neuronal terminals for regulating the neuronal function and content of serotonin, removing serotonin from the synaptic cleft and sending back into the neuronal cytoplasm, where it can be repackaged for reuse or metabolized.

Recent studies show that functions of the serotonergic system are related to different psychiatric and neurological disorders, neurodegenerative disorders, drug addiction, and eating disorders. Neurological disorders include depression, obsessive-compulsive disorder, schizophrenia, anxiety, and autism, and so on. Neurodegenerative disorders include Parkinson's disease, and Alzheimer's disease, and so on. Eating disorders include bulimia nervosa and so on.

In addition, SERTs are also the major targets for antidepressants and anti-obesity drugs, for example, selective serotonin reuptake inhibitors (SSRIs). Studies show that the response to the treatment with these drugs can be predicted according to the availability of SERTs. Even the findings of studies on positron emission tomography (PET) and single photon emission computed tomography (SPECT) show the toxicity of the drug "ecstasy (MDMA)" to serotonergic neurons. Therefore, it is very important to directly detect whether the functions of the human serotonergic system are normal.

Many SERT tracers have been disclosed in the prior art, which are applicable to in-vivo imaging of cerebral neuroreceptors by using PET or SPECT. These SERT tracers include, for example, [$^{11}$C](+)McN5652, [$^{11}$C]SAB, [$^{11}$C]nor-β-CIT, [$^{11}$C]MADAM, [$^{11}$C]AFM, [$^{11}$C]DAPA, [$^{18}$F]ACF, [$^{18}$C] AFM, [$^{123}$I]5-iodo-6-nitroquipazine, [$^{123}$I]IDAM, [$^{123}$I] ODAM, [$^{123}$I]β-CIT, and [$^{123}$I]nor-β-CIT. However, most of the tracers have the disadvantages of undesired specific binding, pharmacokinetics, selectivity, specificity, or signal transduction property. Up to now, I-123-2-([2-({dimethylamino}methyl)phenyl]thio)-5-iodophenylamine ([$^{123}$I]ADAM) is one of the most desirable SERT tracers.

[$^{123}$I]ADAM has a molecular formula of $C_{15}H_{17}N_2SI$, an average molecular weight (calculated based on non-radioactive [$^{127}$I]ADAM) of 385.28, and a chemical structure as shown in FIG. 1(A). The synthesis, purification and analysis methods of [$^{123}$I]ADAM were first developed by Oya et al. from Departments of Radiology and Pharmacology, University of Pennsylvania (Nucl. Med. Biol., 2000, Vol. 27, pp. 249-254). Oya et al. performed a radioiodination through an oxidative iododestannylation reaction to synthesize [$^{123}$I] ADAM under acidic conditions.

In the above oxidative iododestannylation reaction, a tributyltin compound, 2-((2-((Dimethylamino)methyl) phenyl) thio)-5-(tri-n-butyltin)-phenylamine (SnADAM), is used as a precursor. SnADAM has a molecular formula of $C_{27}H_{44}N_2SSn$, an average molecular weight of 547.43, and a chemical structure as shown in FIG. 1(B).

Currently, ADAM (I-123-ADAM and F-18-ADAM) are mainly developed in the laboratories of Departments of Radiology and Pharmacology, University of Pennsylvania, the United States; Karolinska Institute, Sweden; Institute Nuclear Energy Research, National Yang-Ming University, Chang-Gung University, and Chang-Gung Memorial Hospital, Taiwan.

At first, the synthetic product [$^{123}$I]ADAM was purified by complex techniques, such as extraction, drying, and high-performance liquid chromatography (HPLC). However, since the eluent used in HPLC contains a large amount of acetonitrile, it is not suitable for direct injection into the human body. Moreover, since iodine-123 has a half-life ($T_{1/2}$) of only 13.2 hours and a gamma energy of 159 keV, and complex treatment processes need to be used, the risks of drug contamination, radiation dose, degradation of chemical ingredients and decrease in activity of [$^{123}$I]ADAM are increased. Therefore, Institute of Nuclear Energy Research (INER) of Taiwan developed a fast solid phase extraction (SPE), in which the neutralized reactants are directly poured onto an octyl cartridge for purification. Firstly, the cartridge is eluted with water and 50% ethanol to remove the impurities. Then, [$^{123}$I]ADAM is eluted with absolute alcohol for subsequent dilution before use. University of Amsterdam and INER adopt octyl cartridges as the cartridges for fast SPE, and University of Pennsylvania adopts C4 minicolumns (Vydac). There is no significant difference between the elution processes for the octyl cartridges and the C4 minicolumns. The advantages of the fast SPE lie in that, concentrated products can be obtained quickly and automatically labeled, thus reducing the radiation dose received by the personnel.

The purified [$^{123}$I]ADAM is introduced into the human body via intravenous injection and measured by using an SPECT, so as to compare the activity ratio of regions of interest (ROIs) to regions of non-interest (RONIs) (background, BG). The activity ratio is referred to as the specific binding (SB) ratio, as shown in Equation (1):

$$SB = \frac{A_{ROI} - A_{BG}}{A_{BG}}, \qquad (1)$$

in which, $A_{ROI}$ is the region of interest (ROI) radioactivity and $A_{BG}$ is the background (BG) radioactivity.

Up to now, all of the published studies concerning the quality assurance analysis of [$^{123}$I]ADAM are about analytical methods for directly analyzing the radiochemical purity (RCP) of the product [$^{123}$I]ADAM by using HPLC, and none of them provides an analytical method for analyzing the structure and purity of [$^{123}$I]ADAM and its labeled precursor, SnADAM. However, the radioactive RCP analysis can only determine the activities of chemical species containing the radionuclide I-123, including radioactive compounds containing ionic I-123 and I-123 bond, but cannot determine the concentrations of non-radioactive compounds, such as SnADAM and other degradation products and impurities.

The parent molecule [$^{123}$I]ADAM may be fragmented into daughter molecules of different structures due to chemical reaction, especially after [$^{123}$I]ADAM is introduced into the human body. Therefore, it is important to study whether these daughter molecules have side or adverse effects on the human body or not.

SUMMARY OF THE INVENTION

Accordingly, the present invention is directed to a method for analyzing fragmented structures of [$^{123}$I]ADAM and its precursor, SnADAM, to deduce fragmentation pathways of [$^{123}$I]ADAM and SnADAM, so as to further study the effects of the fragmented daughter molecules on the human body.

Further, the present invention is also directed to an analytical method for determining the purity of SnADAM, so as to determine the quality of SnADAM.

As embodied and broadly described herein, the present invention provides an analytical method for determining the purity of SnADAM, including: providing SnADAM, and dissolving SnADAM in methanol; providing a high-performance liquid chromatograph (HPLC), providing a high-performance liquid chromatograph (HPLC), and setting: eluent, methanol/acetonitrile/ammonium acetate solution (10 mM, pH 7.0), 58.8:39.2:2; column temperature, 25° C.; flow rate, 1.0 mL/min, and detection wavelength, 220 nm; chromatographing SnADAM by using the HPLC to obtain a chromatogram; and calculating the ratio of the area of the peak in the chromatogram corresponding to SnADAM to the total area of all peaks in the chromatogram.

The present invention also provides a method for analyzing fragmented structures of SnADAM, including: providing SnADAM, dissolving SnADAM in methanol, and ionizing the parent molecule SnADAM into its parent ion; performing a Q1 scan on the parent ion by using a mass spectrometer, and fragmenting the parent ion into product ions; performing a product ion scan and a precursor ion scan on the parent ion by using the mass spectrometer, to obtain parameters of optimum declustering potential (DP), entrance potential (EP), collision energy (CE), and collision cell exit potential (CXP); providing a high-performance liquid chromatography tandem mass spectrometer (HPLC-MS/MS), and setting: eluent, methanol/acetonitrile/ammonium acetate solution (10 mM, pH 7.0), 58.8:39.2:2; and flow rate, 1.0 mL/min; performing multiple reaction monitoring (MRM) on SnADAM by using the HPLC-MS/MS and setting the parameters of optimum DP, EP, CE, and CXP, to obtain the mass charge ratios (m/z) of MRM transition product ions; and deducing a fragmentation pathway of the parent molecule SnADAM from the m/z of the MRM transition product ions.

The present invention also provides a method for analyzing fragmented structures of [$^{123}$I]ADAM, including: providing [$^{127}$I]ADAM, dissolving [$^{127}$I]ADAM in methanol, and ionizing the parent molecule [$^{127}$I]ADAM into its parent ion; performing a Q1 scan on the parent ion by using a tandem mass spectrometer, and fragmenting the parent ion into product ions; performing a product ion scan and a precursor ion scan on the parent ion by using the tandem mass spectrometer, to obtain parameters of optimum declustering potential (DP), entrance potential (EP), collision energy (CE), and collision cell exit potential (CXP); providing a high-performance liquid chromatography tandem mass spectrometer (HPLC-MS/MS), and setting: eluent, methanol/acetonitrile/ammonium acetate solution (10 mM, pH 7.0), 79.68:19.92:0.40 (v/v/v); and flow rate, 0.4 mL/min; performing multiple reaction monitoring (MRM) on [$^{127}$I]ADAM by using the HPLC-MS/MS and setting the parameters of optimum DP, EP, CE, and CXP, to obtain the mass charge ratios (m/z) of MRM transition product ions; deducing a fragmentation pathway of the parent molecule [$^{127}$I]ADAM from the m/z of the MRM transition product ions; and deducing a fragmentation pathway of the parent molecule [$^{123}$I]ADAM from the fragmentation pathway of the parent molecule [127I]ADAM.

The present invention also provides a method for analyzing the content of SnADAM, including: providing a sample that contains SnADAM; providing a high-performance liquid chromatography tandem mass spectrometer (HPLC-MS/MS), and setting: eluent, methanol/acetonitrile/ammonium acetate solution (10 mM, pH 7.0), 58.8:39.2:2; and flow rate, 1.0 mL/min; performing multiple reaction monitoring (MRM) on the sample to obtain the signal intensity of a particular product ion; and deducing the concentration of SnADAM from the signal intensity of the product ion. The m/z of the MRM transition product ions of the particular product ion are m/z 549.7→m/z 291.1, m/z 549.7→m/z 234.9, m/z 549.7→m/z 197.2, m/z 549.7→m/z 179.5, m/z 549.7→m/z 166.5, m/z 549.7→m/z 123.0, m/z 549.7→m/z 121.0, m/z 178.9→m/z 123.0, m/z 178.9→m/z 121.0, m/z 177.1→m/z 121.0, and m/z 149.1→m/z 121.0.

The present invention also provides a method for analyzing the content of [$^{123}$I]ADAM, including: providing a sample that contains [$^{123}$I]ADAM; providing a high-performance liquid chromatography tandem mass spectrometer (HPLC-MS/MS), and setting: eluent, methanol/acetonitrile/ammonium acetate solution (10 mM, pH 7.0), 79.68:19.92:0.40 (v/v/v); and flow rate, 0.4 mL/min; performing multiple reaction monitoring (MRM) on the sample to obtain the signal intensity of a particular product ion; and deducing the concentration of [$^{123}$I]ADAM from the signal intensity of the product ion. The m/z of the MRM transition product ions of the particular product ion are m/z 385.0→m/z 340.0, m/z 385.0→m/z 212.5, m/z 385.0→m/z 196.5, m/z 385.0→m/z 184.5, m/z 385.0→m/z 180.5, m/z 385.0→m/z 165.6, and m/z 385.0→m/z 152.5.

To sum up, the present invention is an analytical technique for identifying or determining the chemical structures of SERT SPECT imaging agent [$^{123}$I]ADAM and its labeled precursor SnADAM and the chemical purity of SnADAM by using an MS/MS method and an HPLC method. The objective of developing this technique is to check the drug integrity, so as to guarantee the reliability, stability, and high quality of the active component in the SPECT imaging agent for intravenous injection and meanwhile reduce the image interference, background, and the content of impurities (if any) that might compete for transporters.

In order to make the foregoing and other objectives, features, and advantages of the present invention more comprehensible, embodiments are described in detail below with reference to the drawings.

BRIEF DESCRIPTION OF THE DRAWINGS

The present invention will become more fully understood from the detailed description given herein below for illustration only, and thus are not limitative of the present invention, and wherein:

FIGS. 3A-3D are chromatograms of SnADAM subjected to the forced degradation experiment by using an HPLC under different conditions respectively;

DETAILED DESCRIPTION OF THE INVENTION

Figure 1B:
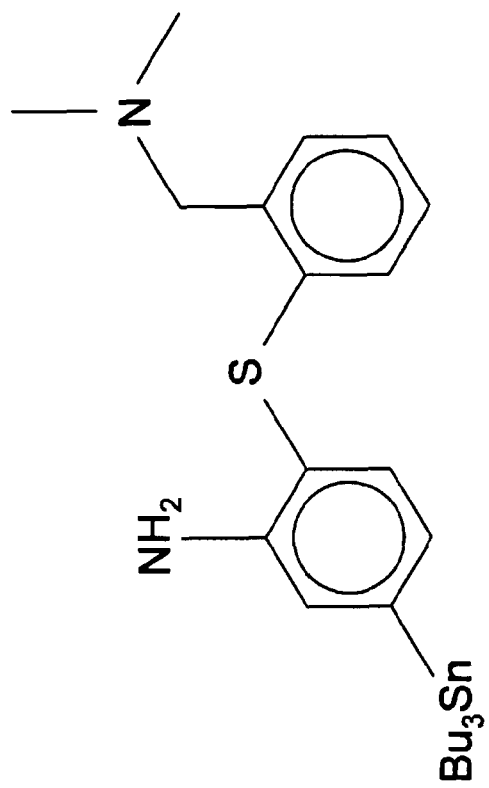
FIG. 1B shows the chemical structure of SnADAM.
Figure 1A:
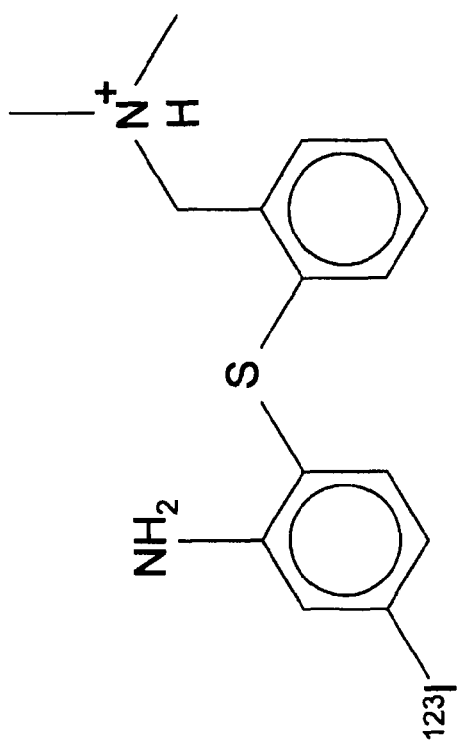
FIG. 1A shows the chemical structure of [$^{123}$I]ADAM.

Hereinafter, a brief introduction is given to instruments, apparatus, reagents, and preparation of standard samples and samples that are needed in the methods of the present invention first, followed by detailed descriptions of the methods for analyzing the structures of [$^{123}$I]ADAM and its precursor, SnADAM, and the purity of SnADAM of the present invention. Minor adjustments may be made to the instruments, apparatus, reagents, and preparation of standard samples and samples to be described below by those skilled in the art with reference to the analytical methods of the present invention, as long as they fall within the scope of the present invention.

Instruments, Apparatus, and Reagents a. High-performance liquid chromatography (HPLC), with column temperature controller and ultraviolet detector.

b. High-performance liquid chromatography tandem mass spectrometer (HPLC-MS/MS), with electrospray ionization (ESI). The HPLC-MS/MS is constituted by an HPLC and a mass spectrometer in tandem for performing multiple reaction monitoring (MRM).

c. Columns:
  (1) For analyzing SnADAM: Chromolith Performance RP-18e, 4.6×100 mm (Merck).
  (2) For analyzing I-ADAM: Zorbox Eclipse XDB-C18, 4.6×50 mm, 1.8 μm (Agilent, USA).

d. Ammonium acetate: analytical grade or reagent grade.

e. Methanol (MeOH): analytical grade or chromatographic grade.

f. Acetonitrile (ACN): analytical grade or chromatographic grade.

Preparation of Standard Samples and Samples a. HPLC analytical solution: At least 10 mg sample is dissolved in MeOH to give a mother solution, which is further diluted with MeOH into sample solutions of different concentrations (10-320 ppm).

b. HPLC-MS/MS analytical solution: About 500 ppm sample MeOH solution is diluted with MeOH to a desired concentration range (1-256 ppb).

First Embodiment

Analysis of the Purity of SnADAM Using HPLC and Validation Experiment for the Analytical Method For this method, when discussing the optimum analytical conditions for HPLC and HPLC-MS/MS, [$^{123}$I]ADAM is replaced by non-radioactive [$^{127}$I]ADAM first. Although [$^{127}$I]ADAM and [$^{123}$I]ADAM have different molecular weights, there is no significant difference between their chemical properties (for example, HPLC retention time). Therefore, the optimum HPLC chromatographic conditions for non-radioactive [$^{127}$I]ADAM are applicable to analysis of [$^{123}$I]ADAM.

Molecular ion masses of components of HPLC chromatographic peaks are determined by using mass spectrometer Q1 scan, and then the structures of the component fragments are determined by using the technology of tandem mass spectrometer precursor ion scan and product ion scan, so as to prove that the components are SnADAM and non-radioactive [$^{127}$I]ADAM (which will be described in detail in Second Embodiment). Since the eluent used for HPLC is a mixed solution of ammonium acetate solution (10 mM, pH 7.0) and MeOH/ACN, the eluent can be directly introduced into the mass spectrometer without causing precipitation, crystallization or ion suppression.

(1) Chromatographic Conditions for Analyzing the Purity of SnADAM

Eluent: MeOH/ACN/ammonium acetate solution (10 mM, pH 7.0)=58.8:39.2:2 (v/v/v)

Column temperature: 25° C.

Flow rate: 1.0 mL/min

Detection wavelength: 220 nm

Figure 2:
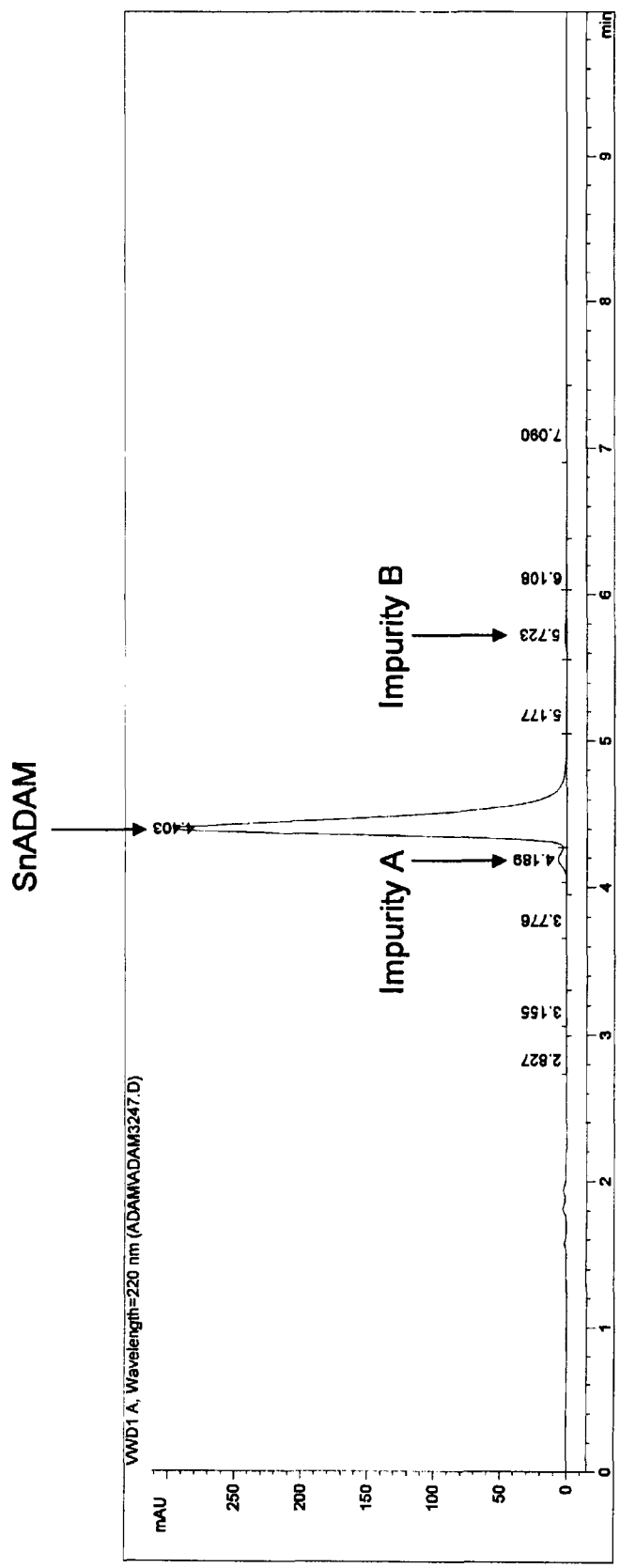
FIG. 2 shows a chromatogram of SnADAM obtained by using a high-performance liquid chromatograph (HPLC)

FIG. 2 shows a typical chromatogram of SnADAM. Referring to FIG. 2, peaks near the retention times ($t_R$) of 4.19 min and 5.72 min are respectively Impurity A and Impurity B, and the peak near the retention time ($t_R$) of 4.40 min, as determined by LC-ESI-MS positive ion mode Q1 scan, is protonated molecular ion ([M+H]$^+$ m/z=549.70) of the main component SnADAM. Likewise, the HPLC position of the protonated molecular ion ([M+H]$^+$) of non-radioactive [$^{127}$I]ADAM can be determined from m/z=385.0.

Referring to FIG. 2, there are mainly two impurities, Impurity A and Impurity B in SnADAM, the chromatographic peak of SnADAM is at the retention time ($t_R$) of 4.40 min, and the chromatographic peaks of Impurity A and Impurity B are at the retention time ($t_R$) of 4.19 min and 5.72 min. The purity of SnADAM can be obtained by calculating the ratio of the area of the chromatographic peak in the chromatogram corresponding to SnADAM (i.e., the area of the chromatographic peak at the retention time of 4.40 min) to the total area of all chromatographic peaks in the chromatogram (i.e., the area of the chromatographic peaks at the retention time of 4.40 min, 4.19 min, and 5.72).

(2) Validation Experiment for the Purity Analysis Method

For the method, the validation experiment for the method for analyzing the purity of SnADAM was carried out according to the requirements of International Conference on Harmonization (ICH), including validating the specificity, linear range and linearity, accuracy, precision, limit of detection/quantification (LOD/LOQ), robustness, and solution stability of the method.

(a) Specificity Experiment

The specificity of the analytical method was demonstrated through the forced degradation experiment. Three portions of 0.50 mg SnADAM were dissolved in MeOH solvent, respectively added with 1 M HCl solution, 1 M NaOH solution, and 3% $H_2O_2$ solution, and then reacted at room temperature for 30 min. The first two portions of solutions were respectively neutralized with 1 M NaOH and 1 M HCl and then added with suitable amounts of MeOH to dissolve the precipitate, while the third portion of solution was directly diluted with a suitable amount of MeOH after the reaction and then subjected to HPLC analysis. Another portion of 0.50 mg SnADAM was heated in an oven at 80° C. for 30 min, dissolved in MeOH solvent, and then subjected to HPLC analysis. The results are as shown in FIGS. 3A-3D. Referring to FIGS. 3A-3D, it is found from the experiment that, the reaction of SnADAM with 1 M HCl solution gave two major degradation products FD1 ($t_R$=1.55 min) and FD2 ($t_R$=1.80 min) (as shown in FIG. 3A). The reaction of SnADAM with 1 M NaOH solution gave a major degradation product FD1 ($t_R$=1.55 min) (as shown in FIG. 3B). The reaction of SnADAM with $H_2O_2$ solution gave a major degradation product FD1 ($t_R$=1.55 min) having the same retention time as $H_2O_2$ (as shown in FIG. 3C). Temperature had little effect on the degradation of SnADAM, so that the reduction in the area of SnADAM was not obvious (as shown in FIG. 3D). Resolutions of SnADAM and the major breakdown products were all greater than 17, showing that the analytical method had a good specificity. Therefore, SnADAM can be separated from the impurities (as shown in FIG. 2) and the degradation products (as shown in FIGS. 3A-3D) without interfering with the quantitative results.

(b) Linearity Experiment

Six SnADAM-MeOH solutions of different concentrations (9.9-317.8 ppm) were prepared and repeatedly subjected to the HPLC experiment three times. Average retention time ($t_R$), integrated area, standard deviation (SD), and relative standard deviation (RSD) of the chromatographic peaks of these concentrations were then calculated. A calibration curve for the concentrations of the main component was plotted by using the average integrated area of the main component at these concentrations, so as to calculate the linear least square regression equation and correlation coefficient (r) of the calibration curve. The results are as shown in Table 1. The linear working range was 9.9-317.8 ppm, the linear least square regression equation was Y=7.83X-6.05, and the correlation coefficient was 1.0000, showing that the analytical method had a suitable working range and a good linearity.

(c) Precision Experiment

The differences between experiments carried out in the same laboratory on different days or by different analysts ware utilized. Six SnADAM-MeOH solutions of different concentrations (9.9-317.8 ppm) were prepared and repeatedly subjected to the HPLC experiment three times. Average retention time ($t_R$), integrated area, standard deviation (SD), and relative standard deviation (RSD) of the chromatographic peaks of these concentrations were then calculated. A calibration curve for the concentrations of the main component was plotted by using the average integrated area of the main component at these concentrations, so as to calculate the linear least square regression equation and correlation coefficient (r) of the calibration curve. Intra-day precision experiments are also called repeatability experiments, and inter-day precision experiments are also called reproducibility experiments.

① The experimental results for intra-day precision are as shown in Table 1. The linear working range was 9.9-317.8 ppm, the linear least square regression equation was Y=7.83X-6.05, and the correlation coefficient was 0.99997. Since more trace impurities may appear as the concentration increases, the purity of the sample was calculated according to the highest concentration (317.8 ppm) within the linear range. The purity (%) of SnADAM was 96.71±0.05 (RSD=0.05%, n=3), the average resolution of SnADAM and the Impurity A ($t_R$=4.19 min) was 1.18±0.06 (RSD=4.75%, n=18), and the average theoretical plate numbers of SnADAM and Impurity A were respectively 7085 and 8198, showing that the method had a good analytical repeatability.

② The experimental results for inter-day precision are as shown in Table 2. For analyses in two days, the difference in retention time was +0.01 min, the difference in purity was +0.23%, and the linear correlation coefficients were all 0.99997, showing that the method had a good analytical reproducibility.

(d) Accuracy Experiment

The accuracy experiment was carried out by using recovery tests. Known amounts (theoretical concentrations of 15.3 ppm, 153 ppm and 306 ppm) of SnADAM were added into MeOH solutions, and subjected to HPLC analysis three times by using the method of the present invention. The experimental values were obtained by interpolation, and recoveries (=experimental values/theoretical values×100%) were calculated. The validation results are as shown in FIG. 3. The average recoveries were 97.18%, 99.12%, and 100.80%.

(e) Lowest Limit of Detection (LOD) and Lowest Limit of Quantification (LOQ):

The lowest LOD and lowest LOQ were respectively calculated by using three times background (S/N ratio=3/1) and ten times background (S/N ratio=10/1). During the method development process, it was found that the major impurity was Impurity A ($t_R$=4.19 min), so the lowest LOD and lowest LOQ for the purity analysis were calculated mainly in consideration of Impurity A as the representative. The average S/N value of Impurity A obtained by the HPLC through analyzing 9.9 ppm SnADAM was 5.40±3.99 (n=3). Therefore, the lowest LOD and lowest LOQ for Impurity A were estimated to be respectively 0.12 ppm±0.07 ppm (RSD=54.28%, n=3) and 0.41 ppm±0.22 ppm (RSD=54.28%, n=3).

(f) Robustness Experiment

The results of experiments carried out with different HPLC columns (with the same brand and model, but from different batches), by different analysts, under different column temperatures, at different eluent pH values, different eluent mixing ratios, and different eluent flow rates were compared, as shown in Table 4.

① Analytical results of different HPLC columns: The difference in the SnADAM retention time was 0.67 min, the difference in purity was 0.57%, the linear regression slopes were all 8, and the linear correlation coefficients were greater than 0.99997.

② Analytical results of different analysts: The difference in the SnADAM retention time was 0.04 min, the difference in purity was 0.64%, the linear regression slopes were all near 8, and the linear correlation coefficients were greater than 0.9997.

③ Analytical results of different column temperatures: The retention time decreased as the temperature was raised, the difference in the SnADAM retention time was −0.19 min, the difference in purity was 0.74%, the linear regression slopes were all near 8, and the linear correlation coefficients were greater than 0.9997.

④ Analytical results of different pH values: There was no significant difference in retention time, purity and linear regression slope, and the linear correlation coefficients were all 0.99997.

⑤ Analytical results of different eluent mixing ratios: When the content of MeOH is increased (53.9%-63.7%), there was no significant difference in retention time, purity and linear regression slope.

⑥ Analytical results of different eluent flow rates: The retention time decreased as the flow rate was increased, but there was no significant difference in purity and linear regression slope, and the linear correlation coefficient was still 1.0000.

(g) Solution Stability Experiment 15.3 ppm, 153 ppm and 306 ppm SnADAM (test sample)-MeOH solutions were prepared and stored at room temperature for three days, and then continuously subjected to HPLC analysis. Meanwhile, a portion of fresh 10-320 ppm SnADAM-MeOH solution is prepared each day to serve as calibration standard sample. The SnADAM chromatographic peak retention time ($t_R$), linear least square regression equation, correlation coefficient (r), purity of the test sample, SD, and RSD of the calibration sample were calculated. The experimental results are as shown in Table 5. Referring to Table 5, the linear correlation coefficients of the fresh calibration standards prepared in three days were all greater than 0.9996. After the test sample was stored at room temperature for three days, the SnADAM retention time RSD=0.31%, and the mean purity RSD=0.05%. It was shown that the SnADAM-MeOH solution had a good stability, and no significant change in purity was observed after stored at room temperature for three days.

TABLE 1

Intra-day Precision for Analysis of the Purity of SnADAM

| Concentration of Sample (ppm) [a] | $t_R$, SnADAM (min) [b] | $t_R$, Impurity A (min) [b] | P (%) [c] |
|---|---|---|---|
| 9.9 | 4.44 ± 0.00 (0.10%) | 4.19 ± 0.00 (0.10%) | — |
| 19.9 | 4.44 ± 0.00 (0.11%) | 4.20 ± 0.01 (0.14%) | — |
| 39.7 | 4.44 ± 0.00 (0.11%) | 4.20 ± 0.00 (0.09%) | — |
| 79.4 | 4.43 ± 0.01 (0.20%) | 4.19 ± 0.01 (0.18%) | — |
| 158.9 | 4.42 ± 0.00 (0.09%) | 4.19 ± 0.00 (0.09%) | — |
| 317.8 | 4.41 ± 0.00 (0.12%) | 4.19 ± 0.00 (0.10%) | 96.71 ± 0.05 (0.05%) |
| N [d] | 7085 ± 124 (1.75%) | 8198 ± 261 (3.18%) | |

[a] Linear ranges of the calibration curve of the six standard samples: 9.9-317.8 ppm, each being repeatedly analyzed three times.
[b] $t_R$: Mean retention time ± SD (RSD, n = 3).
[c] P (%): Purity of SnADAM, average purity (calculated from the analytical results of 317.8 ppm SnADAM) ± SD (RSD, n = 3).
[d] N: Average theoretical plate number ± SD (RSD, n = 18).

TABLE 2

Inter-day Precision for Analysis of the Purity of SnADAM

| $t_{R, SnADAM}$ (min) [a] | P (%) [b] | L eq. [c] | r [d] |
|---|---|---|---|
| 4.43 ± 0.01 (0.31%) | 96.71 ± 0.05 (0.05%) | Y = 7.83X − 6.05 | 0.99997 |
| 4.44 ± 0.02 (0.34%) | 96.94 ± 0.12 (0.12%) | Y = 7.80X + 1.82 | 0.99997 |

[a] $t_{R, SnADAM}$: SnADAM mean retention time ± SD (RSD, n = 18).
[b] P (%): Purity of SnADAM, average purity (calculated from the analytical results of 317.8 ppm SnADAM) ± SD (RSD, n = 3).
[c] L eq.: Linear least square regression equation of the calibration curve of SnADAM, in which linear ranges of the calibration curve of the six standard samples were 9.9-317.8 ppm, each being repeatedly analyzed three times.
[d] r: Linear correlation coefficient of the calibration curve of SnADAM.

TABLE 3

Accuracy for Analysis of the Purity of SnADAM [a]

| Theoretical Value of Unknown Added Sample (ppm) | Experimental Value (ppm) | Recovery (%) [b] |
|---|---|---|
| 15.3 | 14.87 | 97.18 |
| 153.0 | 151.66 | 99.12 |
| 306.0 | 308.44 | 100.80 |

[a] Linear ranges of the calibration curve of the six standard samples: 9.9-317.8 ppm, each being repeatedly analyzed three times. Linear least square regression equation of calibration curve: Y = 7.83X − 6.05; and linear correlation coefficient (r) = 0.99997.
[b] Recovery (%): experimental value/experimental value × 100%.

TABLE 4

Robustness Experiment for Analysis of the Purity of SnADAM

| Item | | $t_{R,SnADAM}$ (min) [a] | P (%) [b] | L eq [c] | r [d] |
|---|---|---|---|---|---|
| Column | #1 | 4.43 ± 0.01 (0.31%) | 96.71 ± 0.05 | Y = 7.83X − 6.05 | 0.99997 |
| | #2 | 5.10 ± 0.07 (1.33%) | 97.28 ± 0.02 | Y = 7.95X + 2.15 | 0.99998 |
| Analyst | #1 | 4.43 ± 0.01 (0.31%) | 96.71 ± 0.05 | Y = 7.83X − 6.05 | 0.99997 |
| | #2 | 4.47 ± 0.03 (0.59%) | 97.35 ± 0.04 | Y = 8.16X − 18.53 | 0.99979 |
| Temp. (° C.) | 25 | 4.43 ± 0.01 (0.31%) | 96.71 ± 0.05 | Y = 7.83X − 6.05 | 0.99997 |
| | 30 | 4.24 ± 0.02 (0.42%) | 97.45 ± 0.01 | Y = 8.16X − 18.53 | 0.99979 |
| pH | 6.5 | 4.40 ± 0.02 (0.34%) | 97.10 ± 0.11 | Y = 7.95X + 2.01 | 0.99997 |
| | 7.0 | 4.43 ± 0.01 (0.31%) | 96.71 ± 0.05 | Y = 7.83X − 6.05 | 0.99997 |
| | 7.5 | 4.40 ± 0.01 (0.29%) | 97.14 ± 0.10 | Y = 7.90X + 2.25 | 0.99997 |
| MeOH:ACN:0.01M NH$_4$Ac (pH 7.0) | 63.7:34.3:2.0 | 4.55 ± 0.03 (0.73%) | 97.18 ± 0.18 | Y = 7.90X − 4.47 | 0.99961 |
| | 58.8:39.2:2.0 | 4.43 ± 0.01 (0.31%) | 96.71 ± 0.05 | Y = 7.83X − 6.05 | 0.99997 |
| | 53.9:44.1:2.0 | 4.83 ± 0.04 (0.85%) | 97.50 ± 0.06 | Y = 7.95X − 6.04 | 0.99966 |
| Flow rate (mL/min) | 0.8 | 5.54 ± 0.02 (0.31%) | 97.18 ± 0.01 | Y = 10.21X − 25.66 | 0.99978 |
| | 1.0 | 4.43 ± 0.01 (0.31%) | 96.71 ± 0.05 | Y = 7.83X − 6.05 | 0.99997 |
| | 1.2 | 3.67 ± 0.01 (0.25%) | 97.49 ± 0.01 | Y = 6.83X − 16.62 | 0.99979 |

[a] $t_{R, SnADAM}$: SnADAM mean retention time ± SD (RSD, n = 18).
[b] P (%): Purity of SnADAM, average purity (calculated from the analytical results f the highest concentration SnADAM standard solution) ± SD (RSD, n = 3).
[c] L eq.: Linear least square regression equation of the calibration curve of SnADAM, in which linear ranges of the calibration curve of the six standard samples were each repeatedly analyzed three times.
[d] r: Linear correlation coefficient of the calibration curve of SnADAM.

TABLE 5

Results of Stability Experiment of SnADAM Solution

| Day | Calibration range (ppm)[a] | L eq.[b] | r[c] | Tested samples (ppm) | Purity of tested samples (RSD, %) |
|---|---|---|---|---|---|
| 1 | 9.9-317.8 | Y = 7.83X − 6.05 | 0.99997 | 15.3 | 98.17 ± 0.17 (0.18%, n = 3) |
|   |           |                  |         | 153.0 | 97.12 ± 0.15 (0.15%, n = 3) |
|   |           |                  |         | 306.0 | 96.77 ± 0.07 (0.07%, n = 3) |
| 2 | 10.1-324.2 | Y = 7.80X + 1.82 | 0.99997 | 15.3 | 98.12 ± 0.21 (0.21%, n = 3) |
|   |           |                  |         | 153.0 | 97.00 ± 0.25 (0.26%, n = 3) |
|   |           |                  |         | 306.0 | 96.73 ± 0.06 (0.06%, n = 3) |
| 3 | 10.0-318.4 | Y = 7.86X − 11.43 | 0.99961 | 15.3 | 97.96 ± 0.73 (0.74%, n = 3) |
|   |           |                  |         | 153.0 | 97.12 ± 0.04 (0.04%, n = 3) |
|   |           |                  |         | 306.0 | 96.70 ± 0.20 (0.20%, n = 3) |

[a]Calibration curve of six standard samples and test samples were each repeatedly analyzed three times.
[b]L eq.: Linear least square regression equation of the calibration curve of SnADAM.
[c]r: Linear correlation coefficient of the calibration curve of SnADAM.

Second Embodiment

Validation of Method for Identifying Structures of SnADAM and [$^{127}$I]ADAM

Chromatographic Conditions for MRM Analysis:
(1) Chromatographic conditions for SnADAM
a. Column: Chromolith Performance RP-18e, 4.6×100 mm (Merck)
b. Eluent: methanol/acetonitrile/ammonium acetate solution (10 mM, pH 7.0)=58.8:39.2:2 (v/v/v)
c. Flow rate: 1.0 mL/min
(2) Chromatographic conditions for [$^{127}$I]ADAM
a. Column: Zorbox Eclipse XDB-C18, 4.6×50 mm, 1.8 μM (Agilent, USA)
b. Eluent: methanol/acetonitrile/ammonium acetate solution (10 mM, pH 7.0)=79.68:19.92:0.40 (v/v/v)
c. Flow rate: 0.4 mL/min In this embodiment, the optimum MRM conditions for HPLC and HPLC-MS/MS were studied by replacing the [$^{123}$I]ADAM samples needed for developing the relative analytical methods by non-radioactive ADAM (i.e., [$^{127}$I] ADAM). Although [$^{127}$I]ADAM and [$^{123}$I]ADAM have a molecular weight difference of 4 Da, the chemical properties, such as HPLC retention time, fragmentation pathway (or fragmentation profile) of parent molecule, and MRM analytical parameters are similar. Then, the optimum analytical parameters obtained for non-radioactive ADAM were applied to MRM analysis in HPLC-MS/MS of [$^{123}$I]ADAM.

In the experiment, firstly, SnADAM or non-radioactive ADAM was directly injected into a mass spectrometer at a flow rate of 10 μL/min by using a syringe pump to perform a Q1 scan, a precursor ion scan, and a product ion scan, so as to obtain the optimum declustering potential (DP), entrance potential (EP), collision energy (CE), and collision cell exit potential (CXP). The optimum results are as shown in Table 6.

In particular, the original state of SnADAM or non-radioactive ADAM may be considered as a parent molecule. Since a mass spectrometer scan is to be performed, the parent molecule needs to be protonated into its parent ion first. However, it can be easily understood by those skilled in the art that, the parent molecule and the parent ion are the same substance in nature. Moreover, product ions fragmented from the parent ion and daughter molecules fragmented from the parent molecule also are the same substances.

Figure 4:
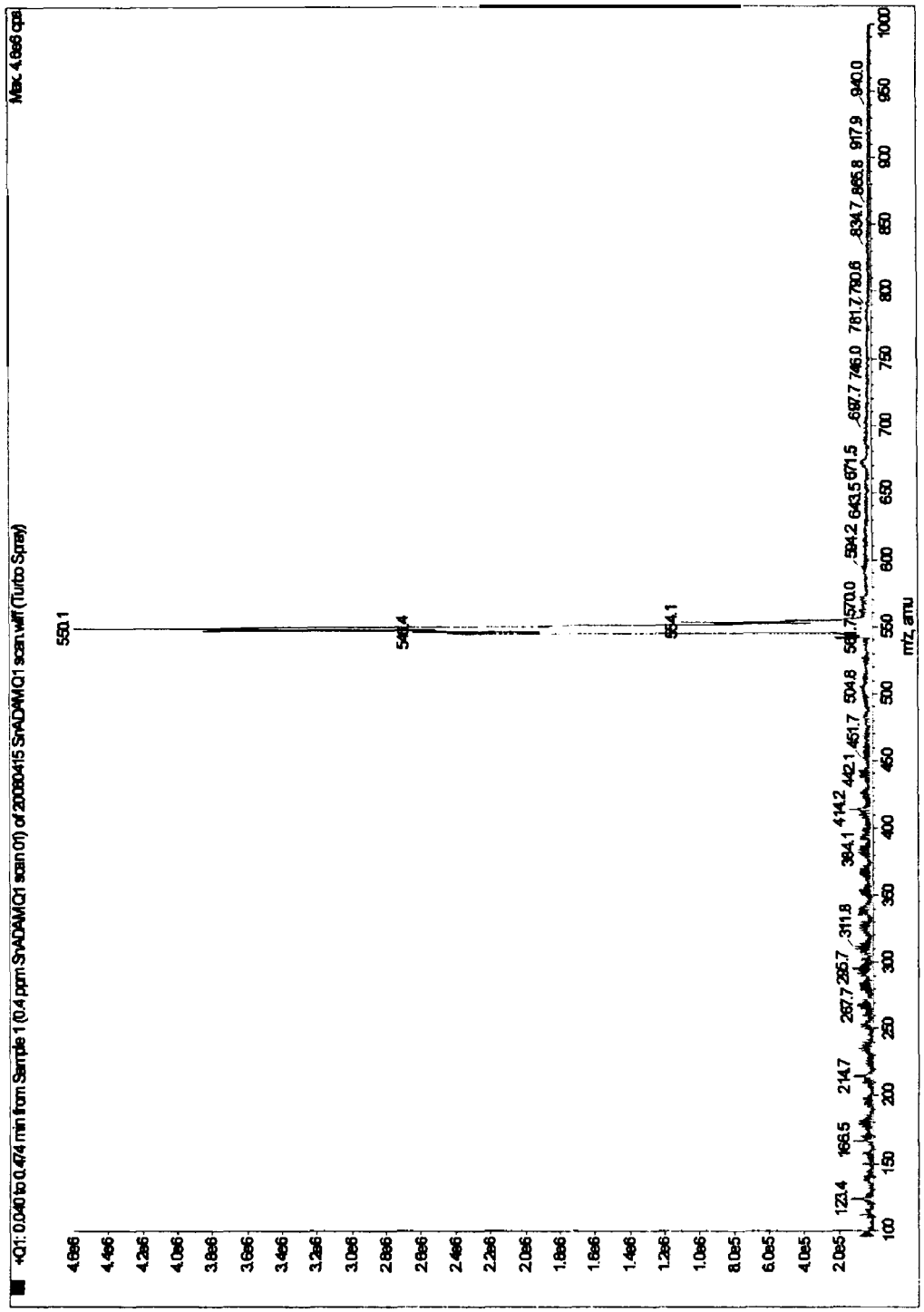
FIG. 4 shows a Q1 mass spectrum of SnADAM.
Figure 5:
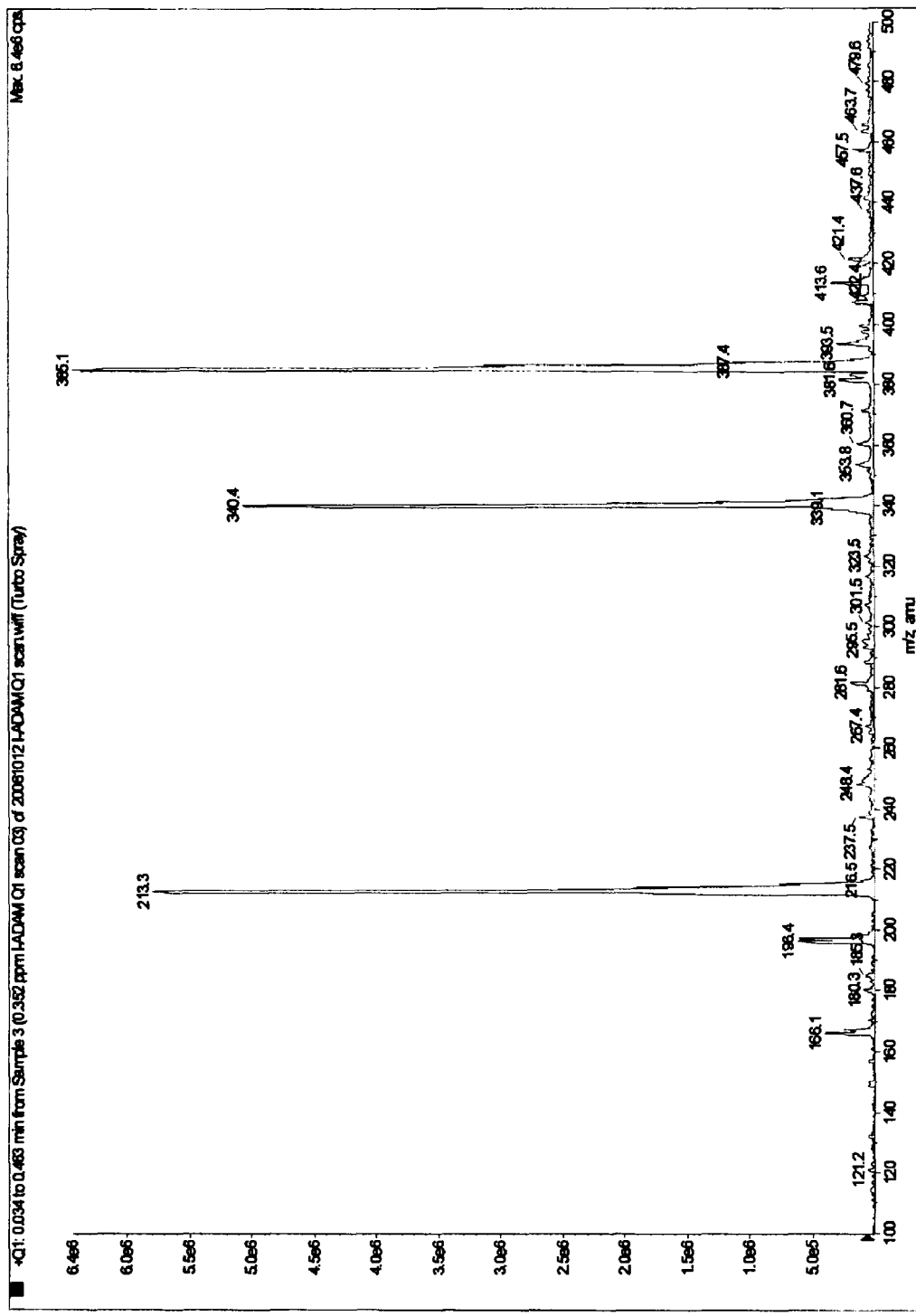
FIG. 5 shows a Q1 mass spectrum of [$^{127}$I]ADAM.
Figure 6:
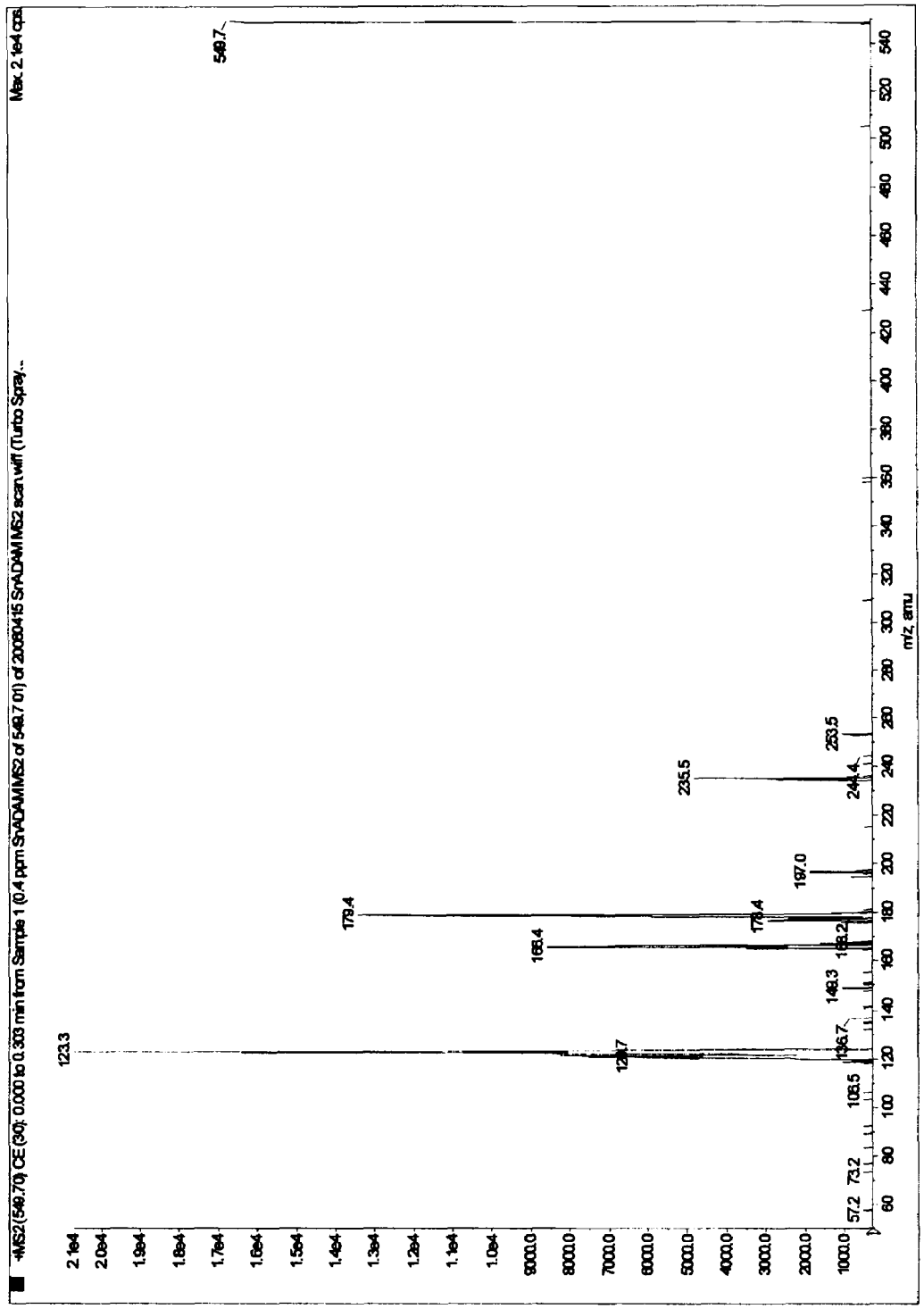
FIG. 6 shows a product ion mass spectrum of SnADAM.
Figure 7:
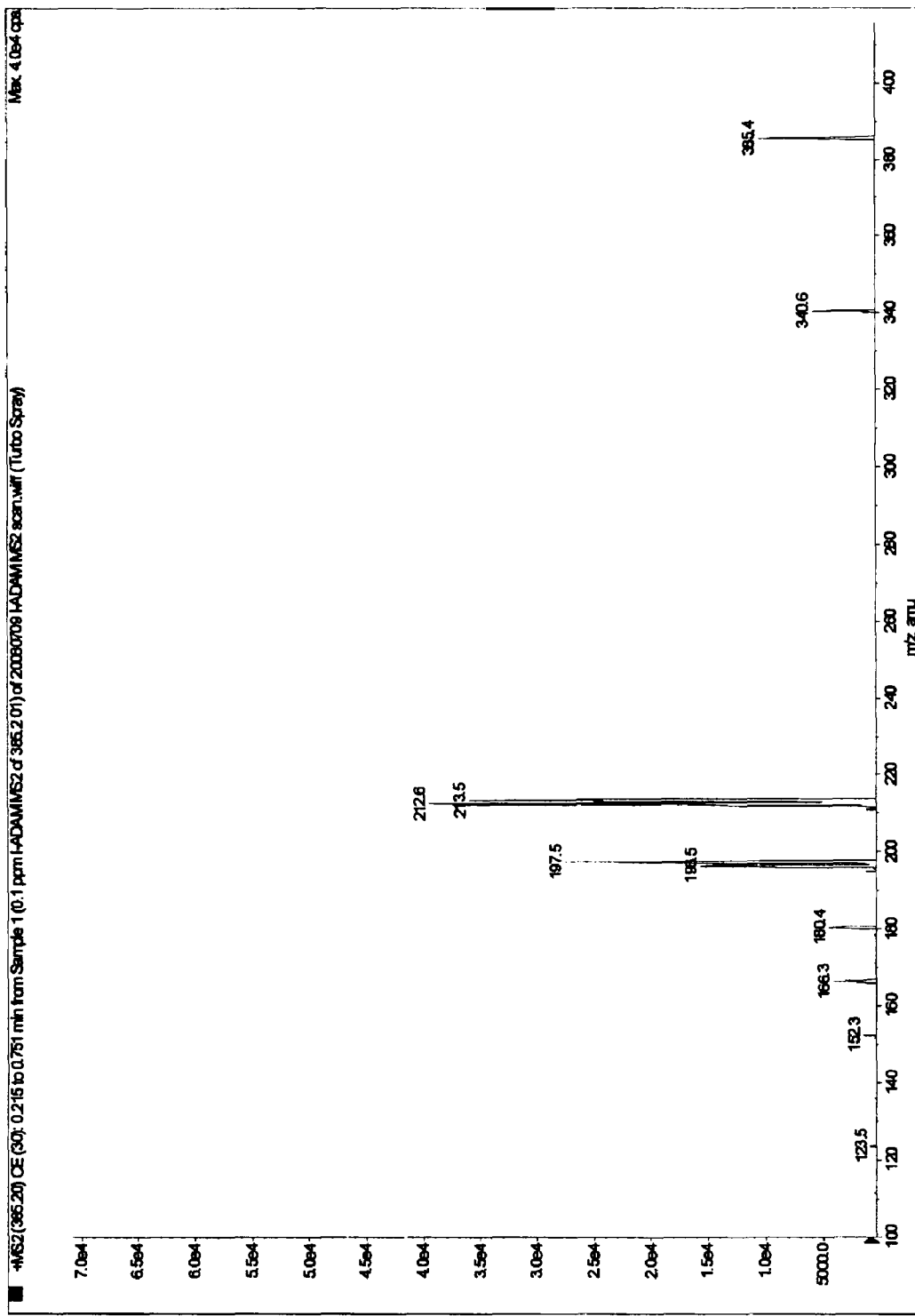
FIG. 7 shows a product ion mass spectrum of [$^{127}$I]ADAM.

The results of the Q1 scan showed that there were no obvious impurities in SnADAM (as shown in FIG. 4) and non-radioactive ADAM (as shown in FIG. 5). It can be found from the results of the precursor ion scan and the product ion scan of SnADAM and non-radioactive ADAM (as shown in FIGS. 6-7) that, the fragmented molecules of SnADAM were mainly m/z 253.5, m/z 235.5, m/z 197.0, m/z 179.4, m/z 166.4, m/z 123.3, and m/z 120.7; and the fragmented molecules of non-radioactive ADAM were mainly m/z 340.6, m/z 212.6, m/z 197.5, m/z 180.4, m/z 166.3, and m/z 152.3, in which m/z represents the mass charge ratio.

In order to prove that the above fragmented molecules are reproducible and are applicable to the quantitative analysis of MRM transitions, the linearity of MRM transitions of SnADAM (m/z 549.7→m/z 291.1, m/z 549.7→m/z 234.9, m/z 549.7→m/z 197.2, m/z 549.7→m/z 179.5, m/z 549.7→m/z 166.5, m/z 549.7→m/z 123.0, m/z 549.7→m/z 121.0, m/z 178.9→m/z 123.0, m/z 178.9→m/z 121.0, m/z 177.1→m/z 121.0, m/z 149.1→m/z 121.0) and non-radioactive ADAM (m/z 385.0→m/z 340.0, m/z 385.0→m/z 212.5, m/z 385.0→m/z 196.5, m/z 385.0→m/z 184.5, m/z 385.0→m/z 180.5, m/z 385.0→m/z 165.6, m/z 385.0→m/z 152.5) was obtained through an experiment by using HPLC as the tool for sample injection under the optimum DP, EP, CE, CXP conditions in Table 6.

The results of the linear least square regression analysis for MRM transitions as shown in Table 7 show that, 14 MRM transitions of SnADAM and 7 MRM transitions of non-radioactive ADAM all have good reproducibility and linearity, and most of the correlation coefficients (r) are greater than 0.995. The MRM transition product ions of SnADAM with the best sensitivity were m/z 549.7→m/z 123.0, m/z 178.9→m/z 123.0, and m/z 177.1→m/z 121.0. The MRM transition product ions of non-radioactive ADAM with the best sensitivity were m/z 385.0→m/z 212.5.

Especially in Table 7, the signal intensities (Y) of the product ions were obtained by HPLC-MS analysis by using SnADAM and non-radioactive ADAM of known concentrations (X), and the relation between the concentrations (X) and the signal intensities (Y) was then calculated by using the linear least square regression. That is, if unknown variables are reversed, unknown concentrations (X) of SnADAM or non-radioactive ADAM can be deduced from the measured signal intensities (Y). In particular, many samples, for example, intravenous injections or biological samples, such as blood, urine, and biological tissue, may contain SnADAM and [$^{123}$I]ADAM. After these samples are preprocessed, the signal intensity (Y) of a particular product ion can be analyzed from the above-mentioned experimental parameters by using HPLC-MS. Then, the concentrations of SnADAM and [$^{123}$I]ADAM can be deduced by using the regression equations in Table 7. This can be easily understood by those skilled in the art, and the details will not be described herein.

It should be noted that, the regression equations in Table 7 are intended to merely illustrate the experimental results under the parameter conditions of this embodiment by way of example, but not to limit the present invention. Any minor modifications to the experimental parameters, instruments, or apparatus still fall within the scope of the present invention.

Figure 8:
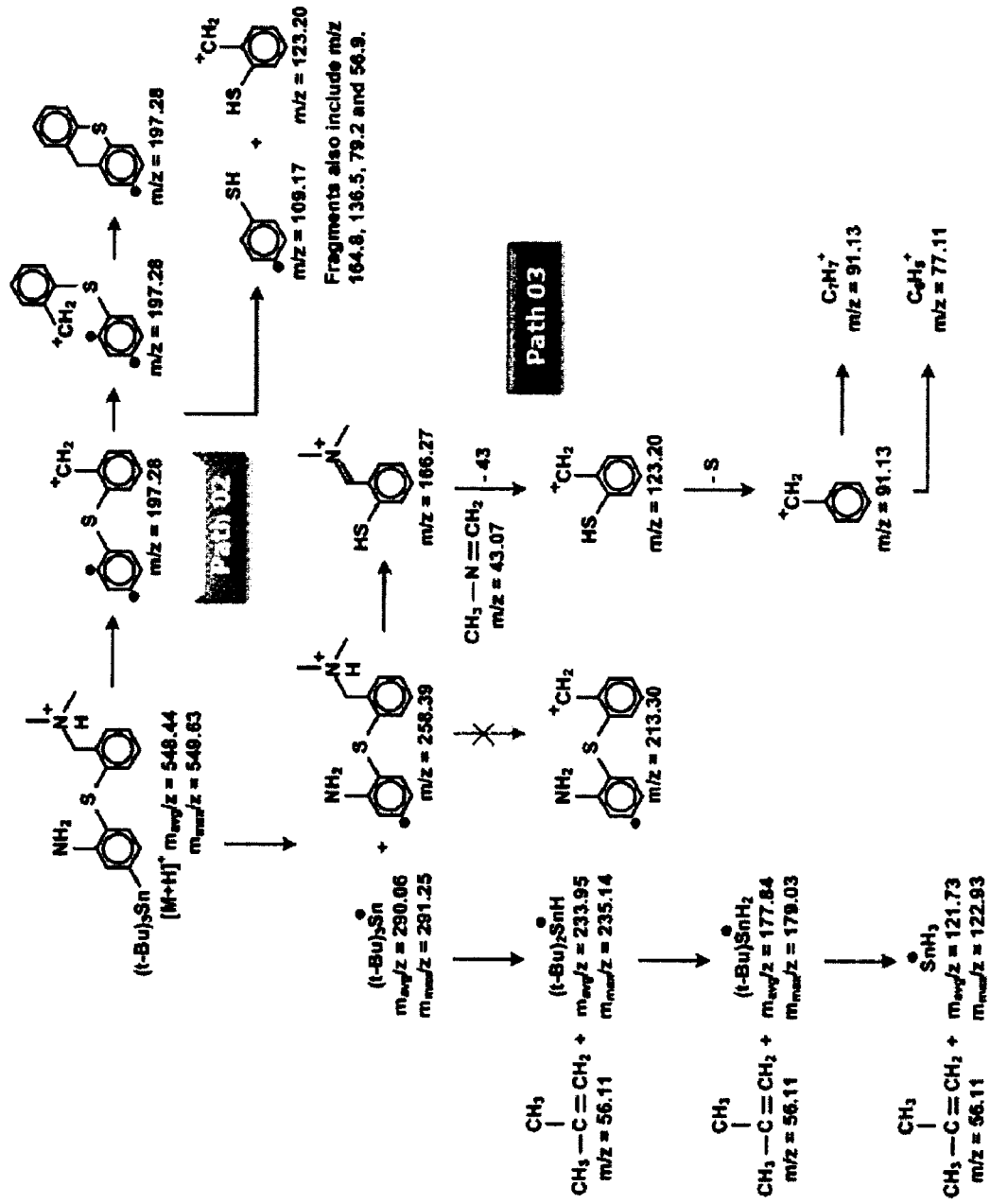
FIG. 8 shows a fragmentation path of the parent molecule SnADAM.
Figure 9:
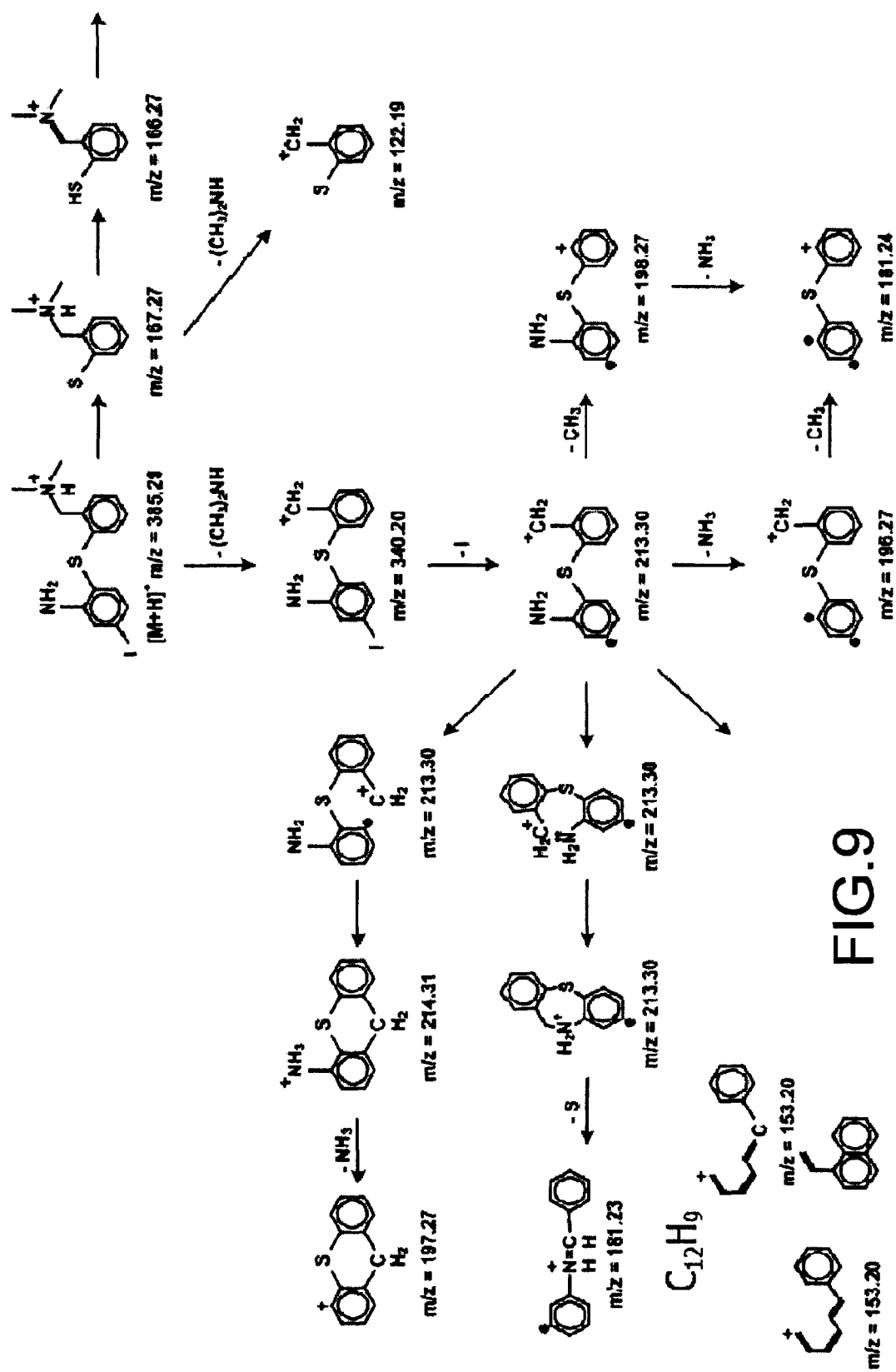
FIG. 9 shows a fragmentation path of the parent molecule [$^{127}$I]ADAM.

It was concluded from the results of the precursor ion scan and the product ion scan of SnADAM and non-radioactive ADAM that, in the fragmentation pathways (or fragmentation profiles) of the parent molecules of SnADAM and non-radioactive ADAM as respectively shown in FIGS. 8 and 9, m/z of most key product ion fragments could be found in the MS precursor ion scan spectrum and product ion scan spectrum.

Figure 10:
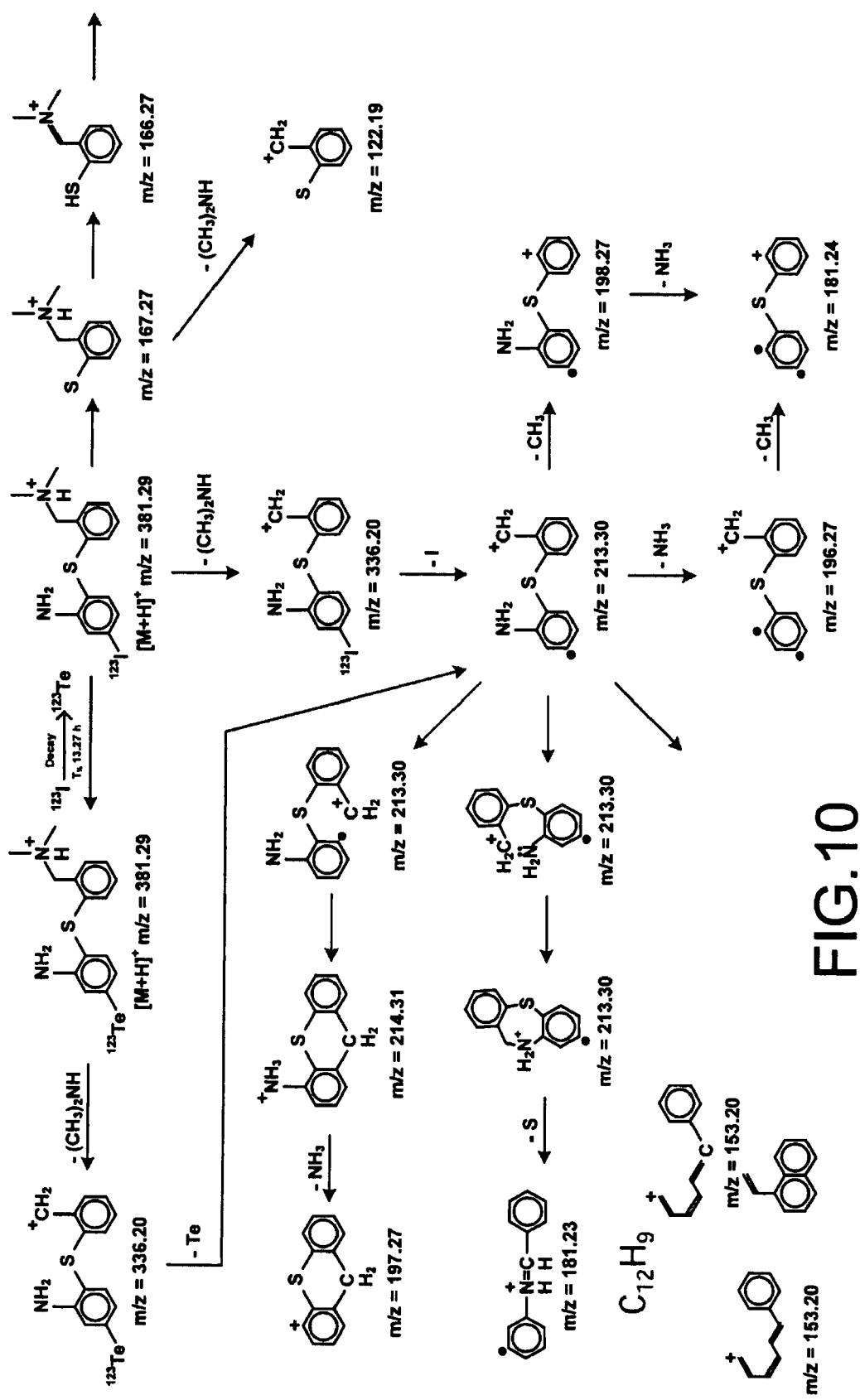
FIG. 10 shows a fragmentation path of the parent molecule [$^{123}$I]ADAM.

Since [$^{123}$I]ADAM and [$^{127}$I]ADAM (i.e., non-radioactive ADAM) have similar chemical behaviors, the fragmentation pathway of the parent molecule of [$^{123}$I]ADAM was further deduced, as shown in FIG. 10.

TABLE 6

Optimum HPLC-MS/MS Analytical Parameters for SnADAM and [$^{127}$I]ADAM

| Compound | $t_R$ (min)[a] | Precursor ion (m/z) | DP[b] | EP[b] | Product ion (m/z) | CE[b] | CXP[b] |
|---|---|---|---|---|---|---|---|
| SnADAM | 4.78 | 549.7 | 105 | 10 | 291.1 | 28 | 18 |
|  |  | 549.7 | 105 | 10 | 234.9 | 31 | 14 |
|  |  | 549.7 | 105 | 10 | 197.2 | 38 | 11 |
|  |  | 549.7 | 105 | 10 | 179.5 | 41 | 9 |
|  |  | 549.7 | 105 | 10 | 166.5 | 28 | 8 |
|  |  | 549.7 | 105 | 10 | 123.0 | 77 | 21 |
|  |  | 549.7 | 105 | 10 | 121.0 | 125 | 20 |
|  |  | 178.9 | 170 | 10 | 123.0 | 16 | 6 |
|  |  | 178.9 | 170 | 10 | 121.0 | 39 | 5 |
|  |  | 177.1 | 171 | 8 | 121.0 | 16 | 6 |
|  |  | 149.1 | 207 | 4 | 121.0 | 8 | 9 |
| I-ADAM | 2.96 | 385.0 | 71 | 13 | 340.0 | 23 | 9 |
|  |  | 385.0 | 71 | 13 | 212.5 | 32 | 12 |
|  |  | 385.0 | 71 | 13 | 196.5 | 50 | 11 |
|  |  | 385.0 | 71 | 13 | 184.5 | 108 | 8 |
|  |  | 385.0 | 71 | 13 | 180.5 | 90 | 9 |
|  |  | 385.0 | 71 | 13 | 165.6 | 26 | 8 |
|  |  | 385.0 | 71 | 13 | 152.5 | 109 | 7 |

[a] $t_R$ (min): HPLC retention time.
[b] DP: Declustering potential. EP: Entrance potential. CE: Collision energy. CXP: Collision cell exit potential.

TABLE 7

Analytical Results of MRM of SnADAM and [$^{127}$I]ADAM

| Compound | MRM ion pair | Linear least square regression equation | r[a] | Linear range |
|---|---|---|---|---|
| Sn-ADAM | 549.7/291.1 | $Y = 5.72 \times 10^1 X + 2.67 \times 10^1$ | 0.9923 | 5-320 ppb |
|  | 549.7/234.9 | $Y = 6.80 \times 10^2 X - 6.32 \times 10^2$ | 0.9998 | 5-320 ppb |
|  | 549.7/197.2 | $Y = 1.69 \times 10^2 X - 6.51 \times 10^2$ | 0.9992 | 5-320 ppb |
|  | 549.7/179.5 | $Y = 3.52 \times 10^2 X - 1.09 \times 10^3$ | 0.9992 | 5-320 ppb |
|  | 549.7/166.5 | $Y = 2.42 \times 10^2 X - 6.87 \times 10^2$ | 0.9992 | 5-320 ppb |
|  | 549.7/123.0 | $Y = 1.20 \times 10^3 X - 1.76 \times 10^3$ | 0.9998 | 5-320 ppb |
|  | 549.7/121.0 | $Y = 3.74 \times 10^2 X - 8.65 \times 10^2$ | 0.9991 | 5-320 ppb |
|  | 178.9/123.0 | $Y = 1.11 \times 10^3 X + 1.13 \times 10^4$ | 0.9980 | 5-320 ppb |
|  | 178.9/121.0 | $Y = 2.03 \times 10^2 X + 2.18 \times 10^3$ | 0.9973 | 5-320 ppb |
|  | 177.1/121.0 | $Y = 1.05 \times 10^3 X + 8.17 \times 10^3$ | 0.9981 | 5-320 ppb |
|  | 149.1/121.0 | $Y = 1.13 \times 10^2 X + 1.95 \times 10^3$ | 0.9965 | 5-320 ppb |
| [$^{127}$I]ADAM | 385.0/340.0 | $Y = 2.88 \times 10^4 X + 3.47 \times 10^5$ | 0.9985 | 8.5-340 ppb |
|  | 385.0/212.5 | $Y = 5.27 \times 10^5 X + 9.55 \times 10^5$ | 0.9957 | 8.5-340 ppb |
|  | 385.0/196.5 | $Y = 2.73 \times 10^4 X + 3.20 \times 10^5$ | 0.9982 | 8.5-340 ppb |
|  | 385.0/184.5 | $Y = 2.65 \times 10^3 X + 2.05 \times 10^4$ | 0.9996 | 8.5-340 ppb |
|  | 385.0/180.5 | $Y = 6.95 \times 10^3 X + 7.67 \times 10^4$ | 0.9984 | 8.5-340 ppb |
|  | 385.0/165.6 | $Y = 5.89 \times 10^3 X + 6.84 \times 10^4$ | 0.9974 | 8.5-340 ppb |
|  | 385.0/152.5 | $Y = 1.44 \times 10^4 X + 1.48 \times 10^5$ | 0.9991 | 8.5-340 ppb |

[a] r: Linear correlation coefficient
X: Concentration
Y: Signal intensity

To sum up, the method for analyzing fragmented structures of SnADAM and [$^{123}$I]ADAM as well as the analytical method for analyzing the purity of SnADAM of the present invention at least have the following advantages.

1. By determining the purity of SnADAM, the quality of SnADAM can be confirmed, which facilitates the subsequent preparation of [$^{123}$I]ADAM.

2. By knowing the fragmentation pathways of SnADAM and [$^{123}$I]ADAM and structures of their daughter molecules, the subsequent studies on their effects on the human body can be carried out.

It will be apparent to those skilled in the art that various modifications and variations can be made to the structure of the present invention without departing from the scope or spirit of the present invention. In view of the foregoing, it is intended that the present invention cover modifications and variations of this invention provided they fall within the scope of the following claims and their equivalents.

What is claimed is:

1. A method for analyzing fragmented structures of [$^{123}$I] ADAM, comprising:

providing a high-performance liquid chromatography tandem mass spectrometer (HPLC-MS/MS);

providing [$^{127}$I]ADAM, dissolving [$^{127}$I]ADAM in methanol, and ionizing the parent molecule [$^{127}$I]ADAM into its parent ion;

performing a Q1 scan on the parent ion by using a mass spectrometer in the HPLC-MS/MS, and fragmenting the parent ion into product ions to find optimum parameters of declustering potential (DP), entrance potential (EP), collision energy (CE), and collision cell exit potential (CXP) when the following m/z of the MRM transition product ions are obtained: m/z 385.0→m/z 340.0, m/z 385.0→m/z 212.5, m/z 385.0→m/z 196.5, m/z 385.0→m/z 184.5, m/z 385.0→m/z 180.5, m/z 385.0→m/z 165.6, m/z 385.0→m/z 152.5;

providing the HPLC-MS/MS and setting: eluent, methanol/acetonitrile/ammonium acetate solution (10 mM, pH 7.0), 79.68:19.92:0.40 (v/v/v); and flow rate, 0.4 mL/min;

performing a multiple reaction monitoring (MRM) chromatography on [$^{127}$I]ADAM by using the HPLC-MS/MS with the parameters of DP, EP, CE, and CXP found above, to obtain mass charge ratios (m/z) of MRM transition product ions;

deducing a fragmentation pathway of the parent molecule [$^{127}$I]ADAM from the m/z transitions of the MRM transition product ions.

2. The method for analyzing fragmented structures of [$^{123}$I]ADAM according to claim 1, wherein the Q1 scan is performed by injecting [$^{127}$I]ADAM into the mass spectrometer at a flow rate of 10 μL/min by using a syringe pump.

3. A method for analyzing a content of [$^{123}$I]ADAM in a sample selected from an intravenous injection, blood, urine, or biological tissue, comprising:

providing a standard sample that contains [$^{127}$I]ADAM at a known concentration;

providing a high-performance liquid chromatography tandem mass spectrometer (HPLC-MS/MS), and setting: eluent, methanol/acetonitrile/ammonium acetate solution (10 mM, pH 7.0), 79.68:19.92:0.40 (v/v/v); and flow rate, 0.4 mL/min;

performing multiple reaction monitoring (MRM) on the sample to obtain signal intensity of the following particular product ions: m/z 385.0→m/z 340.0, m/z 385.0→m/z 212.5, m/z 385.0→m/z 196.5, m/z 385.0→m/z 184.5, m/z 385.0→m/z 180.5, m/z 385.0→m/z 165.6, and m/z 385.0→m/z 152.5;

obtaining a linear regression equation between the concentration of [$^{127}$I]ADAM and the signal intensity of the product ions;

providing a sample that contains [$^{123}$I]ADAM at unknown concentration;

performing multiple reaction monitoring (MRM) on the sample by using the HPLC-MS/MS under the same condition as above to obtain a signal intensity of a particular product ions; and deducing a concentration of [$^{123}$I]ADAM from the signal intensity of the product ion.

* * * * *